United States Patent [19]
Lea

[11] Patent Number: 5,665,391
[45] Date of Patent: Sep. 9, 1997

[54] CULTURED, FULL-THICKNESS INTEGUMENT SUBSTITUTES BASED ON THREE-DIMENSIONAL MATRIX MEMBRANES

[75] Inventor: Peter Lea, Toronto, Canada

[73] Assignee: Spectral Diagnostics Inc., Toronto, Canada

[21] Appl. No.: 542,174

[22] Filed: Oct. 12, 1995

[51] Int. Cl.⁶ ...................................................... A61F 2/10
[52] U.S. Cl. ..................... 424/484; 424/486; 424/488; 424/DIG. 7; 424/400; 623/15
[58] Field of Search .................... 424/484, 486, 424/488, DIG. 7, 574; 623/15; 523/114; 428/315.5

[56] References Cited

U.S. PATENT DOCUMENTS

| | | | |
|---|---|---|---|
| 4,238,571 | 12/1980 | Mano et al. | 521/62 |
| 5,240,862 | 8/1993 | Koenhen et al. | |
| 5,486,593 | 1/1996 | Tang et al. | 528/370 |
| 5,514,378 | 5/1996 | Mikos et al. | 424/425 |

OTHER PUBLICATIONS

Damour et al., Clinical Materials, 15(4), 1994, 273–276.
Kaiser et al., Burns, 20 (1), 1994, 23–29 (Abstract).
MacNeil, Burns, 20 (Suppl. 1), 1994, S67–S70.
Mancini et al., Pediatric Research, 36 (3), 1994, 306–314.
Boyce, Plastic Reconstructive Surgery, 91 (4), 1993, 632–41.
Matouskova et al., Burns, 19 (2), 1993, 118–123 (Abstract).
Ono et al., Burns, 19 (4), 1993, 283–288.
Zhao, Chung Hua Wai Ko Tsa Chih, 31 (4), 1993, 240–1.
Abramo et al., British Journal of Plastic Surgery, 45 (2), 1992, 117–122.
Hansbrough et al., Journal of Burn Care and Rehabilitation, 13, 1992, 519–29.
Hansbrough et al., Surgery (St. Louis), 111 (4), 1992, 438–446.
Harriger et al., Journal of Burn Care and Rehabilitation, 13, 1992, 187–193.
Higashiyama et al., J. of Tokyo Women's Medical College, 62, 1992, 387–395.
Nanchahal et al., British Journal of Plastic Surgery, 45 (5), 1992, 354–363.
Cooper et al., Surgery (St. Louis), 109 (2), 1991, 198–207.
Eldad et al., Burns, 17 (2), 1991, 155–158 (Abstract).
Boyce et al., Surgery (St. Louis), 110 (5), 1991, 866–876.
Yannas, I.V. (1990) Angew. Chem. Int. Ed. Engl. 29:20–35.
Boyce et al., Surgery (St. Louis), 103 (4), 1988, 421–431.
Boyce et al., Journal of Biomedical Materials Research, 22 (10), 1988, 939–958.
Langdon et al., Journal of Investigative Dermatology, 91 (5), 1988, 478–485.
Bell et al., Scanning Electron Microscopy, 1984 (4), 1984, 1957–62.
Kulesz–Martin et al., Scanning Electron Microscopy, 1984 (4), 1984, 1963–1971.

*Primary Examiner*—Edward J. Webman
*Attorney, Agent, or Firm*—Klauber & Jackson

[57] ABSTRACT

A cultured, full-thickness integument substitute is disclosed which can be implanted in a patient suffering from severe burns, for example; and consists of a three-dimensional matrix membrane with essentially two surfaces because the length and width are substantially greater than the thickness; the membrane has pores in the area of a first surface thereof which are directly connected to but substantially larger on average than those in the area of the opposite surface of the membrane, and those pores have immobilized within them cells and components of the dermal layer of the integument; the membrane has pores in the area of a second surface thereof which are directly connected to but substantially smaller on average than those in the area of the opposite surface of the membrane, and those pores have immobilized within them cells and components of the epidermal layer of the integument; the membrane also has a lateral pore structure in its internal space which interconnects those pores which pass from one surface to the other of the membrane, permitting co-planar flow of a liquid or suspension through the membrane.

18 Claims, 3 Drawing Sheets

CULTURED, FULL-THICKNESS INTEGUMENT SUBSTITUTES BASED ON THREE-DIMENSIONAL MATRIX MEMBRANES

FIELD OF THE INVENTION

The present invention is in the field of methods and compositions employed to facilitate and accomplish integument replacement in burn patients and other victims of trauma or any condition that leaves the integument destroyed, so badly damaged that normal recovery is not possible, or vulnerable to invasion by pathogens. The term "integument" as used herein refers to, collectively and individually, the keratinized dead skin cells, the epidermal layer, the basement membrane layer, the dermal layer, and the constituent or component parts thereof, which make up what is known by the less technically accurate term "skin". In fact, the term "skin" can be ambiguous, in that it often refers only to the keratinized dead cell layer, or only to the epidermal layer. The compositions and methods of the present invention also enhance the rate of healing in which the grafted or synthetic integument is applied to the area of damage and grows and becomes integrated into the natural integument layers which still remain. These compositions and methods not only promote healing, but they also improve the quality of the final integument which replaces that lost by the patient, in terms of its flexibility, appearance, pigmentation and sensitivity. Techniques in this field include homo- and heterografts of normal integument, non-integument compositions applied to damaged areas which protect the area and promote regrowth of the patient's integument, and integument substitutes wherein integument cells are cultured on a substrate and the composite final product is applied to the damaged area of a patient and becomes integrated with the patient's own integument. The present invention is concerned especially with the last-mentioned area.

BACKGROUND OF THE INVENTION

As an aid to understanding the following description of the background to the present invention, FIG. 1 shows a schematic view of the integument, including the epidermal and dermal layers thereof, as well as the extracellular matrix, basement membrane, at the interface between those two layers. All of these components of the integument are featured in various methods and articles which have been devised heretofore in an effort to adequately treat patients with severe burn wounds.

I. Semipermeable Burn Dressings

Advantages of Such Dressings

Nonadhesive semipermeable dressings are known to improve the epidermal barrier function without increasing bacterial or fungal colonization in premature infants; and increased cellular proliferation is known to be associated with such improved barrier function in semipermeable dressing-treated fetal integument. See Mancini et al, *Pediatric Research*, 36 (3), 1994, 306–314.

Dressings of Heterologous Collagen Matrix Sponge

Heterologous collagen matrix sponge has been used to prepare third-degree burn wounds for autologous integument grafts. It has been thought that the porosity and multiple connections among the interstices of the sponge enable ready ingrowth of endothelial and inflammatory cells. Heterologous collagen matrix sponge has also been observed to increase the rate of formation of granulation tissue in burn wounds. See Abramo et al, *British Journal of Plastic Surgery*, 45 (2), 1992, 117–122.

Dressings of Omiderm®, a Hydrophilic Polyurethane Film

It is known that wounds which require integument grafts are often heavily contaminated, and heretofore conventional methods of integument grafting have employed bulky dressings. More recently, the concept of an interface has emerged which permits treatment of the wound topically through a transparent, permeable membrane that covers the integument graft without disturbing it. Omiderm®, a hydrophilic polyurethane film that was developed as a burn dressing, has been used as such an interface. See Eldad et al, *Burns*, 17 (2), 1991, 155–158.

Opsite® Semipermeable Polyurethane Integument Graft Donor-site Dressing

It is now well accepted to use semipermeable polyurethane membrane, Op-site®, for integument graft donor-site dressings. It is not only easy to use, even in anatomically difficult areas, but it also maintains a moist environment, allows daily graft observation, and provides a barrier for exogenous bacteria. See Nahas et al, *Plastic and Reconstructive Surgery*, 67 (6), 1981, 791–792.

Implanted Collagen Sponges Injected With Human Uterine Angiogenic Factor

The prime importance of an adequate blood supply to successful grafting of integument and keratinocyte cultures, has long been appreciated, Thus, human uterine angiogenic factor (HUAF) has been employed in this effort, and an extract of HUAF has been injected into subdermally implanted collagen sponges and on sponges implanted into full integument thickness burn wounds. HUAF was found to have induced growth of blood vessels from the surrounding vascular bed into the implanted sponges. See Lindenbaum et al., *Burns*, 15 (4), 1989, 225–229.

Combined Dressing of Silastic Polymer Film and Dermal Substrate Membrane of Porous Atelo-Collagens Immersed in Heparin It is known that heparin accelerates vascularization in the dermis. This has been demonstrated by the covering of wounds infected with methicillin resistant *Staphylococcus aureus* and *Pseudomonas aeruginosa* with artificial membranes composed of silastic polymer films and porous atelo-collagens immersed in a heparin solution. Two weeks after the covering, thin split-thickness integument was grafted on the membrane after removing the silastic polymer film. Histological examination revealed capillary vessels extending to the middle layer of the artificial dermis, as well as the initial process of vascularization. Pseudo-dermination was also observed to be in good condition several weeks after covering. These clinical results have confirmed that heparin employed in this way accelerated vascularization in the dermis, and it has been hypothesized that heparin acts by strengthening, physiologically, the cross-linking among the molecules of the atelo-collagen. See Higashiyama et al, *Journal of Tokyo Women's Medical College*, 62 (4), 1992, 387–395.

II. Integument Substitutes Comprising Artificial Dermal Substrates Which Are Later Epidermalized Made of Collagen GlycosaminoGlycan- (GAG-)Chitosan It is known in cases of severe burns, that it is necessary to debride burnt tissues as soon as possible and to cover the debrided area immediately with a integument substitute, a time at which few autografts are available. Such integument substitutes or dermal substrates have been successfully made of collagen glycosaminoglycan- (GAG-)chitosan which has been grafted immediately after early excision, and then epidermalized with either an autologous meshed autograft or with an autologous cultured epidermis. In such applications, the dermal substrate replaces the excised dermis by adhering to the underlying tissue, thereby promoting fibrovascular ingrowth. After about 15 days, the substrate can be epidermalized with a high rate of success. Epidermalization with autologous cultured epidermis has been found to give the best results. Although such a dermal substrate does not replace the high quality of a homograft, it has been found to be a promising solution for replacement of dermis, since it is always available, can be stored, and is exempt from microorganism transmission. See Damour et al, *Clinical Materials*, 15 (4), 1994, 273–276.

Made of Keratinocyte Culture Suspended in a Fibrin Matrix

The use of cultured epidermal cell sheets has become a recognized method for the coverage of extensive burns. However, significant disadvantages are known to be associated with this use, including a long time-lag before the cells become available; the fragility of the grafts, which makes them difficult to handle; the unpredictability of successful attachment; and the extremely high costs involved. Accordingly, there have been applied to patients with deep partial and full integument thickness burns, cultured autologous keratinocytes suspended in fibrin glue. This keratinocyte culture in a fibrin matrix has then been over grafted with allogeneic, glycerine-preserved, split-thickness cadaver integument. The non-confluent cells have developed a continuous epithelial layer within 4 days, and histological examination has shown a stratified neoepidermis. The new integument has shown satisfactory stability and mechanical quality, and the epidermis of the allogeneic over grafts has desquamated within a few days without signs of inflammation. There have also been indications that the STS-allograft dermis is at least partly integrated into the new integument and may serve as a scaffold for the grafted cell culture. The fibrin glue matrix appears to have given sufficient adherence stability to the keratinocytes which have been grafted in an actively proliferating state. The advantages of this keratinocyte culture in a fibrin matrix have been found to be its ease of application and repetition, as well as a reduction in operating time and costs. See Kaiser et al, *Burns*, 20 (1), 1994, 23–29.

Made of Cultivated Human Keratinocytes on Dried Cell-Free Pig Dermis

It is known that the treatment of full integument thickness burns requires replacement of both the dermal and the epidermal components of the integument. Accordingly, there has been employed a method of preparing recombined human/pig integument by cultivating human keratinocytes on dried cell-free dermis. This dermis culture, dried on a tissue culture dish, has formed a thin collagen film which has behaved like a firm substrate for cell cultures. Human keratinocytes have been grown on the epidermal side of this dermis culture by using lethally irradiated 3T3 cells as feeders. After confluency of human keratinocytes has been reached, human fibroblasts can be cultured on the dermal side of the recombined human/pig integument. It has been possible to obtain approximately 500 cm$^2$ of the recombined integument from 1 cm$^2$ of human split-integument graft in 3 weeks. The recombined human\pig integument has been found to be easy to handle, to be similar in structural, mechanical and adhesive properties to those of normal integument, to be capable of being meshed. See Matouskova et al., *Burns*, 19 (2), 1993, 118–123.

Made of Dermagraft®: a Living Tissue Analog Composed of Human Neonatal Fibroblasts Grown on a Polyglactin Acid Vicryl Mesh There has been an evaluation of the ability of Dermagraft®, from Advanced Tissue Sciences, La Jolla, Calif., to function as a dermal replacement when placed beneath meshed, expanded split-thickness integument grafts. Dermagraft® is a living tissue analog composed of human neonatal fibroblasts grown on a polyglactin acid Vicryl mesh, available from Ethicon Inc., Somerville, N.J. In this evaluation, full-thickness burn wounds in more than a dozen patients have been excised to subcutaneous fat, to fascia, or to a combination of deep dermis and fat. Dermagraft® has then been placed over the experimental sites, after which they have then been covered with meshed, expanded split-thickness integument grafts. Pared controls have received meshed, expanded split-thickness integument grafts only. It has been found that the mesh interstices have epithelialized over the surface of the full-thickness wound in the case of the control sites, and over the surface of the Dermagraft® in the case of the experimental sites. Biopsy specimens have demonstrated no evidence of rejection of the cultured allogeneic fibroblasts and minimal inflammatory reaction to the Vicryl fibers. Evidence of continuous basement membrane formation at the epithelial-Dermagraft® junction, which has been identified by immunohistochemical staining for laminin and type IV collagen, has been seen by day 14 beneath the healed epithelium in the integument graft interstices. The Vicryl fibers were observed to have hydrolyzed in the wound over a 2-to-4 week period, although some expulsion of fibers has occurred as the healing epithelium has advanced to close the interstices of the meshed, expanded slit-thickness integument grafts. Elastic fibers have not been seen in neodermal tissue in either control or experimental wounds at periods of up to 1 year after grafting. See Hansbrough et al, *Journal of Burn Care and Rehabilitation*, 13 (5), 1992, 519–529.

Made of Cross-linked Collagen and Glycosaminoglycan Or A Collagen Matrix Populated by Allogeneic Keratinocytes Currently, split-thickness autografts offer the best form of wound coverage, but limited donor sites and their associated morbidity have prompted the search for alternatives. The application of allogeneic integument grafts is limited by availability and the risk of the transmission of infection, while synthetic integument substitutes can often be little more than expensive dressings. The problem of limited expansion may be overcome by culturing keratinocytes in vitro. Unlike autologous cells, allogeneic keratinocytes are available immediately. The absence of a dermal component in these grafts predisposes them to instability and contracture. A cross-linked collagen and glycosaminoglycan dermal substitute, covered with thin split-integument grafts or cultured autologous keratinocytes, has shown promise in burn patients. An alternative is a collagen matrix populated by allogeneic keratinocytes. See Nanchahal et al, *British Journal of Plastic Surgery*, 45 (5), 1992, 354–363.

Made of Polyglycolic Acid or Polyglactin-910 Mesh Containing Confluent, Cultured Human Fibroblasts It has been recognized that meshed, expanded split-thickness integument grafts frequently achieve poor results when they are used to cover full-thickness wounds. These poor cosmetic and functional results have been considered to occur in part because the epithelium that grows across the interstices of a integument graft lacks a dermis. In order to overcome these problems, a living dermal replacement has been created which is composed of either polyglycolic acid (PGA) or polyglactin-910 (PGL) mesh containing confluent, cultured human fibroblasts. These grafts have been applied to full-thickness wounds and subjected to periodic histologic examination. It has been found that the PGN/PGL-fibroblast graft has vascularized to the wound, and that the meshed, expanded split-thickness integument graft has simultaneously vascularized to the PGA/PGL-fibroblast graft. Epithelialization from the meshed, expanded split-thickness integument graft bridges proceeds rapidly across the surface of the PGA/PGL-fibroblast graft, resulting in an epithelialized layer that covers a densely cellular substratum that resembles dermis. Basement membrane formation at the dermal-epithelial junction of the epithelialized interstices has been confirmed by immunohistochemical microscopy. It has been found that grafts composed of PGA or PGL biodegradable meshes combined with cultured fibroblasts vascularize in full-thickness wounds, resulting in the formation of organized tissue beneath the epithelialized surface that resembles dermis. See Hansbrough et al, *Surgery (St. Louis)*, 111 (4), 1992, 438–446.

III. Integument Produced With a Dermal Substrate, Or Without a Substrate

Epithelialized Sliced Dermal Sheets Using Epidermal Growth Factor

Sliced dermal sheets from human patients have been stretched with one surface stuck on the base of a culture dish, and then incubated in Dulbecco's essential medium for tissue culture, to which epidermal growth factor has been added. After one week, only the upper side has been epithelialized from epithelial components in the sliced dermis, and the formation of basement membrane with anchoring fibrils has been confirmed by electron microscopy. The appearance of type IV collagen and laminin has been observed between epithelialized basal cells and the dermal layer. Thus, the sliced dermal grafts have been considered useful not only for immediate grafting, but also as a substitute for free split thickness integument grafts following tissue culture. See Ono et al., *Burns*, 19 (4), 1993, 283–288.
Made at an Air-Liquid Interface It is known that human keratinocytes grown in a integument equivalent at an air-liquid interface demonstrate differentiation approaching that of human integument when analyzed morphologically and biochemically. Within 3 weeks of growth at such an interface, cuboidal basal cells, distinct spinoud and granular zones, and a fully developed cornified layer of enucleated cells will have formed the multilayered epidermis. Ultrastructurally, the keratinocytes in the upper granular layer will have been found to contain tonofilament bundles and membrane-coating granules. These cells will have formed cornified squames that are resistant to degradation by sodium dodecyl sulfate/dithiothreitol. Basal cells will have become attached to a developing basement membrane with hemidesmosomes. Immunogold silver staining analysis with monoclonal antibodies will have demonstrated the expression of basement membrane collagens IV and VII. This level of differentiation is speculated to have improved the adhesion of human grafts, and is considered to have provided a useful system with which to study topical carcinogens and tumor promoters in vitro. See Harriger et al, *Journal of Burn Care and Rehabilitation*, 13 (2 part 1), 1992, 187–193.
Substrate of Self-Assembled Collagen Fibrils With Fibroblasts Incorporated into the Lattice What has been referred to as the living integument equivalent is a tissue formed when self-assembled collagen fibrils are contacted by fibroblasts, and that the rate and extent of the volume contraction of this composite is proportional to the number of cells incorporated into the lattice. The fibroblasts are biochemically active in the lattice, synthesizing collagen and adding it to the matrix. This compacted lattice provides a substrate allowing attachment of keratinocytes and the formation of a multilayered keratinized epidermis with a basement lamella. When a integument equivalent grafted to a recipient animal is wounded, it is capable of wound contraction and repair. Because of the simplified character of the integument equivalent, it may offer a useful model for studying wound healing, as well as transplantation reactions. Results obtained on the persistence of allografted fibroblasts in the rat have been viewed as supporting the theory that fibroblasts are antigenically neutral. See Bell et al., *Scanning Electron Microscopy*, 1984 (4), 1984, 1957–1862.
Cultured Integument Substitutes Cultured integument substitutes have been compared directly to treatments with murine integument autograft, human integument xenograft, or no graft. Ultrastructural examination of wounds with cultured human integument 6 weeks after treatment have shown complete basement membrane, including anchoring fibrils, the presence of melanocytes and pigment transfer to keratinocytes, and the innervation of healed integument adjacent to the basement membrane. Such findings are recognized as demonstrating the effectiveness of cultured integument substitutes for the closure of integument wounds, and illustrating their important capabilities for modulating the natural processes of wound repair, for increasing the supply of materials used for wound repair, and for enhancing the quality of wound healing. See Hansbrough, *Surgery (St. Louis)*, 110 (5), 1991, 866–876.
Human Dermis as a Source of Human Collagen It is known that a source of human collagen is discarded human dermis collected after integument grafting, from which the collagen is extracted by using a pepsin-controlled degradation method. Under vacuum and freezing conditions, white-clear, frothy, pliable collagen membrane of human dermis can be obtained. The collagen membrane can be stored easily, transported readily, and used under normal temperature conditions. The collagen membrane has a spongiform structure and has improved water-permeability, adhesiveness, and flexibility, with less antigenicity. See Zhao, *Chung Hua Wai Ko Tsa Chih*, 31 (4), 1993, 240–1.
Optimized Integument Cell Culturing Using an Automatic Perfusion, Rocker Culture Apparatus It has been possible to achieve long term growth and differentiation of adult human integument cells by more effective control of culture pH, osmolarity and nutrient supply at optimized set point values, than with conventional batch feed culture. This control has been achieved by means of an automatic perfusion, rocker culture apparatus. The multilayered outgrowth has maintained a predominantly epithelial cell composition, but has contained normal integument cell types other than keratinocytes, including melanocytes and dermal fibroblasts. Neither mouse feeder cells, nor the selective pressures of passage have been required to obtain growth in surgically useful quantities. See Kulesz-Martin et al, *Scanning Electron Microscopy*, 1984 (4), 1984, 1963–1972.

IV. Completely Synthetic Integument Composites

Composites of Autologous Cultured Epidermis and Allogeneic Dermis

Grafts of allogeneic dermis and autologous epidermal cell cultures have been used to replace extensively burned integument. The final grafts are thus composites of autologous cultured epidermis and allogeneic dermis. Reconstitution of the dermal-epidermal (BMZ.1) and microvascular (BMZ.2) basement membrane zones has been studied immunohistochemically and ultrastructurally. At day 76, BMZ.1 has revealed only small hemidesmosomes, few incipient anchoring fibrils, and a discontinuous lamina densa. BMZ.2, however, has been fully reconstituted. By day 124, both BMZs appear normal. Observations in the dermis at day 76 have included the presence of lymphocytes, organellar debris, and hyperactive collagen fibrillogenesis, all indicative of dermal remodeling. The microvasculature has been found to be well differentiated, but no elastic fibers or nerves have been found. In the epidermis, melanocytes and evidence of melanosome transfer have been seen up to day 95 after grafting of the keratinocyte cultures. Based on these observations, it has been concluded that the composite procedure reconstitutes integument with excellent textural and histologic qualities. See Langdon et al, *Journal of Investigative Dermatology*, 91 (5), 1988, 478–485.

Composite of Human Keratinocytes Attached to a Collagen and Chondroitin-6-Sulfate Dermal Replacement There has been demonstrated the in vitro formation of biologic attachments between human keratinocytes and a collagen and chondroitin-6-sulfate dermal integument replacement. Dermal membranes have been prepared as generic acellular sheets and stored in the dry state for extended periods. Subconfluent human keratinocyte cultures in logarithmic phase growth can attach quickly to dermal membranes in vitro, form a confluent epithelial sheet on the surface of each membrane, and exhibit mitotic cells for at least 1 week. Transmission electron microscopy reveals the formation of hemidesmosomes, extracellular matrix, and banded collagen at the interface of the epidermal cells and the dermal membrane. By comparison, human keratinocyte cultures as confluent sheets released enzymatically with Dispase, do not attach to the dermal membranes in vitro, although complete coverage of the membrane by the cell sheets is obtained. Growth assays show that subconfluent human keratinocyte cells retain sufficient growth potential to maintain logarithmic phase growth, but that human keratinocyte cells disaggregated from confluent sheets become growth arrested in comparison. The composite material has discrete dermal and epidermal compartments, has a total thickness comparable to split-thickness integument graft, and can be applied to full-thickness integument defects in a single procedure. See Boyce et al., *Surgery (St. Louis)*, 103 (4), 1988, 421–431.

Matrix of Type I Collagen Crosslinked with a Glycosaminoglycan, Having Cultured Human Fibroblasts Seeded into Its Interstices, And Cultured Human Keratinocytes Applied to Its Surface It has been recognized that wound coverage may be accelerated if the integument can be expanded to produce an integument replacement that reproducibly supplies blood to the wound and has good structural qualities. Seeking a way to achieve that objective has lead to the development of a composite integument replacement composed of cultured human keratinocytes and fibroblasts. Cultured human fibroblasts are seeded into the interstices, and cultured human keratinocytes are applied to the surface of a matrix composed of type I collagen crosslinked with a glycosaminoglycan, which has a defined physical structure. After the human keratinocytes reach confluence on the matrix surface, the composite grafts are placed on full-thickness wounds of subjects. Graft acceptance is about 90%. A defined integument structure is present histologically by day 10 after grafting, with a differentiated epithelium and a subepidermal layer densely populated by fibroblasts and capillaries without evidence of inflammation. Fluorescent light microscopy identifies laminin and type IV collagen, and electron microscopy confirms the presence of basement membrane components by 10 days after grafting. Attachment of the grafts to the wound is found to be similar with and without the addition of human basic fibroblast growth factor, a potent angiogenic agent, to the integument replacement before graft placement on the wounds. See Cooper et al., *Surgery (St. Louis)*, 109 (2), 1991, 198–207.

Collagen-Glycosaminoglycan Substrates Populated With Cultured Dermal Fibroblasts and Epidermal Keratinocytes Composite grafts consisting of collagen-glycosaminoglycan substrates populated with cultured dermal fibroblasts and epidermal keratinocytes have been tested on full-thickness burn wounds as an alternative to split-thickness integument. Light microscopy and transmission electron microscopy have shown regeneration of epidermal and dermal tissue by 2 weeks, with degradation of the collagen-glycosaminoglycan implant associated with low numbers of leukocytes, and deposition of new collagen by fibroblasts. Complete basement membrane, including anchoring fibrils and anchoring plaques, has been formed by 2 weeks, is mature by 3 months, and accounts for the absence of blistering of healed epidermis. See Boyce, *Plastic Reconstructive Surgery*, 91 (4), 1993, 632–41.

Collagen and Glycosaminoglycan Membrane Substrates Optimized for Pore Size

It is known to optimize the structure of dermal substitutes, e.g., collagen and glycosaminoglycan membrane substrates for cultured human epidermal keratinocytes, for pore size in order to promote ingrowth of fibrovascular tissue from the wound bed and to enhance culture of the human keratinocytes on the membrane's surface. Pore size of the freeze-dried material is regulated by control of the temperature of freezing between −50° C. and −20° C. and by concentration of the starting materials between 0.17% and 1.62% wt/vol. A nonporous surface of collagen-GAG has been laminated to the membranes to provide a planar substrate for the cultured epidermal keratinocytes. The thickness of the dermal substitutes has been regulated by control of the volume and concentration of the starting materials. Biotin has been conjugated to solubilized collagen for binding with avidin of specific quantities of biologically active molecules. See Boyce et al, *Journal of Biomedical Materials Research*, 22 (10), 1988, 939–958.

V. Role of the Extracellular Matrix

Extracellular Matrix Influence on Keratinocyte/Fibroblast Biology

There are strong indications that the major role of the extracellular matrix (ECM) is in regulating cell/cell communication, rather than in passively supporting cells. There are suggestions that specific arrangements of sequences within the ECM profoundly influence the behavior of the cells moving in that area, with respect to attachment, migration, differentiation and proliferation. In the integument, the ECM is thought to promote appropriate communication between the keratinocyte and the fibroblast. Integument ECM can be considered to consist both of the large insoluble proteins produced primarily by the fibroblasts, and soluble proteins which may be produced by fibroblasts or keratinocytes, and become attached to the ECM. Both the large insoluble and the smaller soluble proteins are thought to constitute signals which influence the behavior of the keratinocytes. There is a clinical awareness of the need for a dermal component in integument grafting, and thus of the importance of knowing the way in which the ECM influences keratinocyte/fibroblast biology. Such knowledge will shed light on the problems of graft take, graft contracture and scarring. See MacNeil, *Burns*, 20 (Suppl. 1), 1994, S67–S70.

Synthetic Extracellular Matrix Analogues

It is known that during the course of development, the extracellular matrices, which are complex macromolecular networks, are typically broken down enzymatically to oligopeptides and are then resynthesized (remodeled) to form insoluble and nondiffusible macromolecular structures which confer stability of shape to multicellular systems. Mature extracellular matrices such as the integument, provide stiffness and strength to tissues and organs. Remodeling also occurs in adult organisms, during wound healing. An understanding of the role that extracellular matrices play during wound healing can be obtained by the use of synthetic extracellular matrix analogues. A few of these have been found to possess remarkable biological activity, inducing partial regeneration of integument and peripheral nerve. These analogues are graft copolymers of collagen and chondroitin 6-sulfate, a glucosaminoglycan, in the state of highly hydrated and covalently cross-linked gels. These copolymers are synthesized so as to afford adjusted physicochemical properties, such as the rate at which they degrade enzymatically when implanted, the elements of their pore structure, and the degree of collagen crystallinity. Since biological activity appears only when the physicochemical parameters fall within very narrow limits, it has been conjectured that what is involved is a single insoluble growth factor which is specific for integument synthesis. See Yannas, *Angewandte Chemie International Edition in English*, 29 (1), 1990, 20–35.

SUMMARY OF THE INVENTION

Figure 1:
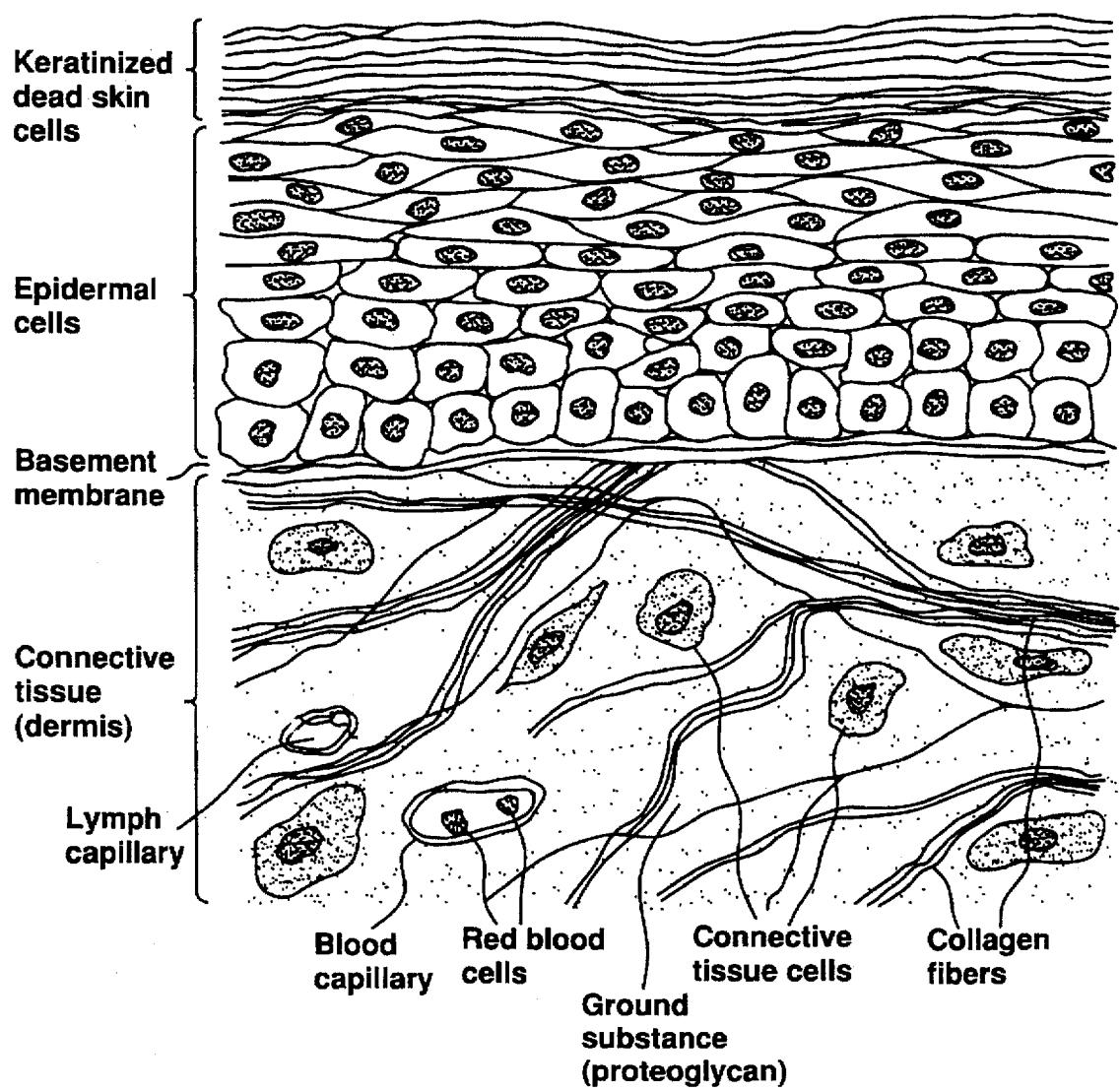
FIG. 1 is a schematic view of integument tissue showing the epidermal and dermal layers thereof, as well as the basement membrane or extracellular matrix.

The present invention relates to a cultured, full-thickness integument substitute implanted in or to be implanted in a patient requiring the same, comprising a three-dimensional matrix membrane with essentially two surfaces, in that the length and width thereof are substantially greater than the thickness thereof, and which is non-reactive with respect to the cells and components of said integument; said membrane having pores in the area of a first surface thereof which are directly connected to but substantially larger on average than those in the area of the opposite surface of said membrane, having a mean pore diameter in the range of from about 50 µm to about 900 µm, said pores having immobilized therein cells and components of the dermal layer of said integument; said membrane having pores in the area of a second surface thereof which are directly connected to but substantially smaller on average than those in the area of the opposite surface of said membrane, having a mean pore diameter in the range of from about 0.5 µm to about 100 µm, said pores having immobilized therein cells and components of the epidermal layer of said integument; said membrane also having a lateral pore structure in the internal space thereof interconnecting said pores which pass from one surface to the other of said membrane, permitting co-planar flow of a liquid or suspension therethrough.

The present invention further relates to a cultured, full-thickness integument substitute implanted in, or to be implanted in a patient requiring the same, comprising a three-dimensional matrix membrane wherein said membrane is made from a material which is non-reactive not only with respect to the cells and components of said integument, but also with respect to the tissues of the patient in whom it is to be implanted. Said material may be a natural or synthetic polymer or a mixture of both. In particular, said material is collagen or a derivative thereof, such as a graft copolymer of collagen and a glycosaminoglycan selected from chondroitin-6-sulfate, chondroitin-4-sulfate, heparin sulfate, heparin, dermatan sulfate, and keratan sulfate, of which chondroitin-6-sulfate is preferred.

The present invention also relates to a cultured, split-thickness integument substitute for either the dermal layer or for the epidermal layer, implanted in, or to be implanted in a patient requiring the same, comprising a three-dimensional matrix membrane with essentially two surfaces, as described further above, but in which either the pores in the area of said first surface have immobilized therein cells and components of the dermal layer of said integument, or in which the pores in the area of said second surface have immobilized therein cells and components of the epidermal layer of said integument. The matrix membrane with only dermal layer cells and components may be implanted in a patient having, e.g., a full-thickness burn, where the membrane will become anchored to the patient's supporting tissue sublayers exposed by said burn, while the epidermal layer may be supplied in a number of ways, e.g., as a simple homograft. The exposed outer or top surface of said matrix membrane will be said second surface, in the area of which the smaller pores occur, thus providing a hospitable environment in which the applied layer of epidermal cells and components can thrive.

Indeed, while it is sometimes preferred to have already carried out a substantial amount of the culturing of the dermal and/or epidermal cell layers within the matrix membrane before it is implanted in a patient, virtually to the point of confluence, the matrix membrane, nevertheless, provides a favorable framework within which the dermal and epidermal cells and components can not only prosper in terms of growth in absolute numbers, i.e., proliferation, but within which the crucial aspects of tissue formation can take place, i.e., differentiation, Consequently, it is contemplated to be a part of the present invention to provide the integument substitute as solely a three-dimensional matrix membrane as described herein, as a cultured, full-thickness integument substitute having a full complement of integument components present in levels at or near the capacity of said matrix membrane, or as an integument substitute anywhere between those two extremes. The integument substitute, no matter what the stage of culturing to which it has progressed, may be implanted in the patient, where the culturing process will be completed.

The present invention further relates to a surgical kit comprising a sealed container providing a sterile environment, and contained therein a sterilized surgical implant device comprising a cultured, full-thickness integument substitute to be implanted in a patient requiring the same, wherein said three-dimensional matrix membrane has immobilized within the cells thereof dermal layer cells and components, and/or epidermal layer cells and components, as described further above.

The present invention still further relates to a method of preparing a cultured, full-thickness integument substitute to be implanted in a patient requiring the same, comprising the steps of A) establishing a three-dimensional matrix membrane with essentially two surfaces, in that the length and width thereof are substantially greater than the thickness thereof, and which is non-reactive with respect to the cells and components of said integument; said membrane having pores within the area of a first surface thereof which are directly connected to but substantially larger on average than those in the area of the opposite surface of said membrane, having a mean pore diameter in the range of from about 400 µm to about 900 µm; said membrane having pores in the area of a second surface thereof which are directly connected to but substantially smaller on average than those in the area of the opposite surface of said membrane, having a mean pore diameter in the range of from about 0.5 µm to about 100 µm; said membrane also having a lateral pore structure in the internal space thereof interconnecting said pores which pass from one surface to the other of said membrane, permitting co-planar flow of a liquid or suspension therethrough; B) bringing said first surface of said matrix membrane with said larger pores in contact with cells and components of said integument whereby they pass through said matrix membrane, with the larger cells and components of the dermal layer of said integument becoming immobilized within the pores in the area of said first surface of said matrix membrane, and with the smaller cells and components of the epidermal layer of said integument becoming immobilized within the pores in the area of said second surface of said matrix membrane; C) culturing said matrix membrane thus seeded with said cells and components of said integument immobilized in different pore layers thereof under conditions favorable to growth of said integument cells, whether in vivo or in vitro, whereby there results a cultured, full-thickness integument substitute already implanted in, or ready for implantation in said patient.

The present invention further relates to the method of preparing a cultured, full-thickness integument substitute in accordance with the procedures described above, wherein instead of having all of the cells and components of said integument suspended in a culture or nutrient medium which is passed through the matrix membrane, so that the various cells are separated by being trapped in different pore layers, and then become established in the different pore layers, they are segregated into dermal layer cells and components suspended in a medium, and epidermal layer cells and components suspended in a medium; and instead of the medium being passed through only one side of said matrix membrane, the dermal layer medium is passed through the said first surface with the larger pores, while the epidermal medium is passed through said second surface with the smaller pores. This modification of the basic process permits the use of different sources for each layer of integument. Thus, the source of the epidermal layer portion can be the patient, thus giving a homograft, while the source of the dermal layer portion can be other than the patient, thus giving an allograft. With regard to the basic process itself, this same distinction applies, of course, with all of the cells and components of said integument, epidermal and dermal, being entirely from the patient, or entirely from other than the patient.

DETAILED DESCRIPTION OF THE INVENTION

As set out further above, the present invention relates to cultured, full-thickness and split-thickness integument substitutes to be implanted in a patient requiring the same.

Full-thickness and Split-thickness

There can be a large variety of reasons why such a patient would be in need of such a full-thickness or split thickness integument substitute. Before exploring those reasons, however, it should first be pointed out that the term "full-thickness" is a term of art meaning essentially both layers of integument, i.e., the dermal layer and the epidermal layer, and that it is used herein as having the same meaning. However, while the term "split-thickness" is used in the art to refer to only one of said layers of integument, the epidermal layer, it has been given an expanded meaning herein, and is used to refer to either the epidermal or the dermal layer of integument, with reference to the integument substitutes of the present invention.

The three-dimensional matrix membrane used in the present invention provides many unique advantages. One of these is that the integument substitute which is implanted in the patient can be the three-dimensional matrix membrane by itself; or it can be the cultured, full-thickness integument substitute having a full complement of integument components present in levels at or near the capacity of the matrix membrane; or it can be any integument substitute which can be created between those two extremes. The integument substitute, no matter what the stage of preparation to which it has progressed, may be implanted in the patient, where the ongoing process of cell multiplication and differentiation will be completed. This affords the significant advantage of reducing or eliminating the criticality attached heretofore to the stage of maturity which an integument substitute had reached, and whether it and the patient were ready for the implantation. Accordingly, the terms "full-thickness" and "split-thickness" are used herein only as approximations of the stage of development of the integument substitutes of the present invention, and largely refer to the presence of epidermal and/or dermal cells.

The focus herein on the epidermal and dermal cell layers of the integument substitutes of the present invention should not detract from the other cell types which are also present and an important part of the integument substitutes. These other cell types include the basement membrane, which arises at the interface between the epidermal and dermal cell layers and genetically becomes responsible for their further proliferation; the components of the extracellular matrix, which can affect or control cell attachment, migration, differentiation and proliferation; fibroblasts, which promote the process of growth and vascularization; and melanocytes, which provide the desired pigmentation in the integument substitute. All of these cells can be added in different combinations and at different times. For example, once the epidermal layer has been established in the three-dimensional matrix membrane of the present invention, basement membrane cells can then be added and allowed to proliferate. Dermal layer cells are added next. Included with these additions to the matrix membrane may be any one or more of the other above-enumerated cell types.

Sources of Integument Damage Necessitating Integument Replacement

The most prevalent reason for a patient to require a full-thickness or split-thickness integument substitute to be implanted is a severe burn which has effectively destroyed the patient's integument, both the epidermal and the dermal layers thereof, which will usually have occurred over a sizable portion of said patient's body. However, there are other, less frequent events which may cause extensive and deep damage to the integument, e.g., damage originating from contact with toxic chemicals, especially concentrated acids and alkalies, exposure to strong sources of irradiation, accidents involving machinery in which the flesh may be badly injured or torn away, extensive damage caused by exposure to extreme cold, severe injury sustained from disease, and destruction from microbial sources, such as the so-called flesh-eating bacteria (*Staphylococcus sp.*). While some of these sources of destruction and damage may tend to confine their effects to the epidermal layer, of concern here is the destruction of both the dermal and epidermal layers.

Whatever the source of injury, this type of deep integument destruction has long been a treatment challenge to the medical and surgical communities. The difficulties entailed have largely been with respect to two areas of concern. First, the integument is the natural barrier which the patient has to a hostile outside world of pathogens, and this barrier has suddenly been breached. Its speedy restoration is, therefore, essential. Second, the integument is composed not only of the epidermal and dermal layers, but of other components as well, including vascularization elements and the basement membrane between the epidermal and dermal layers. All of these are essential to healed integument which is truly restored, i.e., which gives good cosmetic and functional results.

Multiple Integument Components

This has been a notable problem with meshed, expanded split-thickness integument grafts which have been used extensively in the past. The epithelium that grows across the integument graft interstices lacks a dermis. However, where cultured human fibroblasts in a biodegradable polymer mesh have been used as a dermal replacement for full-thickness wounds, with a meshed, expanded split-thickness integument graft over it, vascularization, epithelialization, and basement membrane formation has been observed. Thus, the three-dimensional matrix membrane of the present invention offers a single, composite framework within which multiple components of the integument can be immobilized and grown, promoting both proliferation and differentiation. Moreover, the phenotype of a cell is very strongly influenced by the immediate environment of that cell, regardless of its genotype; and the three-dimensional matrix membrane of the present invention has been found to uniquely duplicate the normal environment of the integument, especially of the epidermal layer, to a high degree, thus permitting and facilitating the required development.

It will be understood from the above description that where the three-dimensional matrix membrane of the present invention is being used as a split-thickness integument substitute, that the matrix membrane still affords all of the above-referred to advantages. When the matrix membrane is implanted in the patient, all of the patient's integument layer components will grow through the matrix membrane and their proliferation and differentiation will be promoted in the same way.

It will also be understood that the term "integument substitute" does not necessarily imply that the dermal, epidermal, or other cells thereof are from a source other than the patient, i.e., are a 100% allograft. As already indicated, the integument substitutes of the present invention can be 100% homograft, 100% allograft, or any combination between those extremes. Further, the term "integument substitute" does not mean that the present invention is concerned with articles and methods which involve materials which are wholly artificial, man-made, non-natural, synthetic, or any other term denoting them as being from a source which is other than natural. The term is one frequently employed in the art, and is used here for that reason and with the same meaning, i.e., an integument replacement for grafting, comprising one or more cultured integument components, optionally in a polymer mesh or matrix.

Three-Dimensional Matrix Membrane: Essentially Two Surfaces

The three-dimensional matrix membrane of the present invention has essentially two surfaces, i.e., the length and width thereof are substantially greater than the thickness thereof. This aspect of the matrix membrane is wholly in accord with its function as part of a composite to be implanted in a patient as a integument substitute or replacement. Like the integument which it is replacing, it is a membrane, i.e., a thin, soft, pliable sheet. This membrane is "implanted" in a patient, a term used in the art with respect to integument grafting, although "engrafted" could be used as well.

The first two dimensions of the matrix membrane, the length and width, are determined either by the restrictions and conveniences of manufacturing the membrane, or by the demands of the market place, or both. The lateral area of the matrix membrane may be determined as well by the actual dimensions of the burn or wound area of the patient into which the matrix membrane integument substitute is to be implanted. It should be pointed out that one advantage of the matrix membrane integument substitute of the present invention is that it can be cut to fit the required dimensions of the patient's burn or wound, simply by using surgical scissors, preferably under aseptic conditions.

The demands of manufacturing and the marketplace may require a matrix membrane in the range of from about 1 cm by about 1 cm, all the way up to about 100 cm by about 100 cm or more. Preferably, the length and width dimensions will be from about 5 cm to about 50 cm, and more preferably from about 10 cm to about 25 cm. The matrix membranes do not have to be square in shape, and may preferably be in the shape of rectangular strips. Neither do they have to be rectilinear, but may have various rounded contours from circles to ovals and any combinations of these with rectilinear forms. Whatever the shape and dimensions, however, there will always be two objectives: to minimize the number of adjoining edges or joints which are created when more than one segment of integument substitute is employed to cover a wound or burn area of the patient; and to maximize the coverage afforded by any one particular segment of integument substitute. The third dimension of the matrix membrane, the thickness, is substantially less that the other dimensions, and is, in fact, more appropriately measured in millimeters. Thus, the thickness will be from about 0.1 mm to about 5 mm, preferably from about 0.5 mm to about 3 mm, and more preferably from about 1 to about 2 mm.

Three-Dimensional Matrix Membrane: Mean Pore Diameter, Pore Volume Fraction, and Specific Surface Equally, if not more important than the three dimensions described above for characterizing the matrix membranes of the present invention are the mean pore diameter, the pore volume fraction, and the specific surface of the matrix membranes. These give a much more accurate reflection of the dimensions of the matrix membranes which are actually being used in the formation of the integument substitute, i.e., the size of the pores, what fraction of the total matrix membrane volume is occupied by those pores, and the total surface area of all of those pores. In the area of the first surface of the matrix membrane, where the pores are directly connected to but substantially larger on average than those in the area of the opposite, i.e., second surface, the mean pore diameter will be in the range of from about 50 µm to about 900 µm, preferably from about 500 µm to about 800 µm, more preferably from about 600 µm to about 700 µm. In the area of the second surface of the matrix membrane, where the pores are directly connected to but substantially smaller on average than those in the area of the opposite, i.e., second surface of said membrane, the mean pore diameter will be in the range of from about 0.5 µm to about 100 µm, preferably from about 5.0 µm to about 50 µm, more preferably from about 10 µm to about 40 µm.

The pore volume fraction will be up to about 0.996, i.e., up to about 99.6% of the total volume of the matrix membrane will be occupied by the voids and spaces which comprise the pores or porous structure of the matrix membrane. Alternatively, 0.4% or more of the total volume of the matrix membrane will be occupied by the material from which the matrix membrane is actually constructed. It is preferred that the pore volume fraction be from about 0.990 to about 0.995, and more preferably from about 0.992 to about 0.994, since it has been found that the non-porous component of the matrix membrane provides a favorable framework within which the dermal and epidermal cells and other components of the integument can prosper in terms of proliferation and differentiation.

The specific surface of the matrix membrane, measured in terms of square millimeters (mm$^2$) of area per gram of matrix membrane, can vary significantly, depending upon the mean pore diameter and the pore volume fraction, and provides a measurement of the surface which is available for immobilization, adherence, proliferation and differentiation of the dermal and epidermal cells and other components of the integument. The specific surface of the matrix membrane of the present invention will range from about $10^3$ to about $10^9$ mm$^2$ per gram of matrix membrane, preferably from about $10^4$ to about $10^8$ mm$^2$ per gram of matrix membrane, and more preferably from about $10^5$ to about $10^7$ mm$^2$ per gram of matrix membrane.

Three-Dimensional Matrix Membrane: Non-Reactive, Strong, Durable, Flexible, and Preferably Bio-Degradable The matrix membrane of the present invention is "non-reactive" with respect to the cells and components of the integument for which it provides a framework. The term "non-reactive" as used herein does not mean that the matrix membrane is totally inert. Indeed, there is an expected physical interaction between the cells and other components of the integument and the matrix membrane in terms of the mechanisms by which the integument components become immobilized within the pores of the matrix, possibly develop an adherence thereto, followed by a fostering of their proliferation and differentiation in some manner. These activities may have a chemical component as well. It is clearly necessary that the integument components and the matrix membrane interact. By "non-reactive" on the other hand, is meant that there will not take place any type of strong, co-valent chemical reaction which substantially changes the properties of the matrix membrane or the integument components, or both, especially in a manner which negatively affects the use of the composite matrix membrane and integument components as a integument substitute.

In addition to being non-reactive and having the three-dimensional porous structure described elsewhere, it is also necessary that the three-dimensional matrix membrane used in the present invention have sufficient durability, flexibility and strength to provide a framework for proliferation and differentiation of the integument cells and components which will retain its desirable characteristics during the culturing process, during the implantation process, and during the healing process, during most of which there will be a considerable amount of manipulation of the matrix membrane, particularly during the implantation process.

The remaining characteristic of the matrix membrane captioned above, bio-degradability, is in reality an optional, although preferred, characteristic. In certain situations, it may be desirable, even necessary, to prepare the matrix membrane from a material which has no bio-degradability at all. One such situation would be where the additional structural support provided by a persistent synthetic polymer framework was required for the reconstructive surgery and healing of the patient's wound or burn. Because of the very high pore volume fractions of the matrix membranes used in the present invention, the very small percentage of polymer material present, e.g., as little as 0.5%, and less than that amount, once healing is complete, make it entirely possible to implant these synthetic polymer materials in the body of the patient and allow them to become a permanent part of the healed integument of said patient. There is now an attitude of acceptance on the part of the general population toward the implantation of such totally foreign materials that would make such procedures feasible. Of course, it is also necessary to sound a cautionary note by pointing out that as a matter of prudence, the artisan will find it necessary to investigate the properties of any candidate synthetic polymer with respect to its antigenicity or potential toxicity or tendency to cause an inflammatory responses in patients, even in a relatively small percentage of normal patients, before proceeding with construction of a three-dimensional matrix membrane using such a synthetic polymer.

Three-Dimensional Matrix Membrane: Preselected Pore Structure Using an Integrated Polymer Structure Comprising a Hydrophobic Polymer Matrix with a Hydrophilic Polymer Attached Polymeric materials of various kinds, both natural and synthetic, may be used to construct the matrix membrane. It has been found, e.g., that hydrophilic microporous membrane materials are suitable, which may consist of a hydrophobic polymer matrix to which is attached a hydrophilic polymer. The hydrophilic polymer while in an essentially non-swollen state may be attached to the hydrophobic polymer framework by cross-linking. An integrated polymer structure is thereby created, the pore structure of which may be adjusted accurately, permitting one to tailor the membranes to certain desired specifications. The hydrophobic polymer may be selected from polyethylene, polypropylene, polytetrafluoroethylene, polyacrylonitrile, polyvinylidene mono- and difluoride, polyethylene vinylacetate, and polyester; while the hydrophilic polymer may be selected from nitrocellulose, hydroxypropylcellulose and other cellulosic materials and derivatives, collagen and collagenous materials and derivatives, polyvinyl pyrrolidone, polycarbonate, polysulfone/poly(ether sulfone), polyimide/poly(ether imide), and aliphatic polyamide. Where it is desired to prepare a biodegradable matrix membrane, polymers of the type above can be employed which have introduced therein individual monomers, or segments, or blocks of monomers which are susceptible to degradation by agents to be encountered in a patient's dermal tissues, e.g., enzymes, oxidizing agents, microbes, etc.

The matrix membranes of the present invention are integral asymmetric membranes; the term "integral" being used to indicate that both the top layer and the sublayer consist of the same material. These membranes are prepared by known phase inversion techniques; thus, the hydrophobic polymer material which is selected must be soluble in a solvent or solvent mixture, although this is seldom a problem. Once the hydrophobic polymer component of the matrix membrane is thus formed, the hydrophilic polymer component is then added. This is achieved by crosslinking of the hydrophilic and hydrophobic components, with the assistance of cross-linking agents. The choice of polymer materials will determine which cross-linking agents are suitable, but these are well known to the artisan.

Three-Dimensional Matrix Membrane: Using a Template Process to Prepare an Integrated Polymer Structure Comprising Collagen and Derivatives Thereof A preferred choice for the starting material from which to make the hydrophilic component of the three-dimensional matrix membrane, is collagen and derivatives thereof, since it is a naturally occurring composition which is a constituent of the integument. However, collagen and its derivatives are not especially well suited to preparing three-dimensional matrix membranes in accordance with the method described further above, wherein the preselected pore structure can be created by using an integrated polymer structure comprising a hydrophobic polymer matrix with a hydrophilic polymer attached thereto. Consequently, there has been devised in accordance with the present invention a novel method for preparing the desired matrix membranes from collagen and its derivatives which is simple, accurate and efficient. This method is based on the template principle, i.e., using the surface contours of one object to essentially replicate those contours in a second surface. This method is not, strictly speaking, a "lost wax", photographic, or similar process in which a negative master is used to produce an exact duplicate positive. However, the method of the present invention retains sufficient similarities to such processes, that it will be referred to herein as a template method. In accordance with that method, a three-dimensional matrix membrane is first prepared which has an integrated polymer structure comprising a hydrophobic polymer matrix with a hydrophilic polymer attached, and has the desired characteristics in terms of the range of pore dimensions therein.

There is next applied to this matrix membrane, acting as a substrate, a suspension of the desired collagen or collagen derivative composition. The suspending solvent passes through the matrix membrane, leaving the collagen or collagen derivative composition trapped in the pores of the matrix membrane. Because of the particle size and other characteristics of the collagen and collagen derivative compositions, e.g., the conformation produced by the long chain character of those compositions, the pore structure of the matrix membrane will not be occluded, but only partially filled. The essential three-dimensional makeup of the matrix membrane remains intact, including importantly, the incremental change in pore diameter from surface to surface. After the collagen or collagen derivative composition is applied to the matrix membrane, a drying process follows, which may be accelerated by the application of heat and air currents, or vacuum. Once the collagen or collagen derivative is firmly adhered to the matrix membrane, the thus coated matrix membrane may be used in the manner described throughout the instant specification. After the collagen or collagen derivative coated matrix membrane is used, e.g., to separate and immobilize epidermal cells therein, the three-dimensional matrix membrane which forms what amounts to a skeleton for the collagen or collagen derivative composition lattice which has been formed by coating, may be removed by simply separating it from the collagen lattice through the application of physical forces in opposite directions. This result is achievable because of the essentially two-dimensional nature of the matrix membrane and the collagen lattice adhered thereto.

It is biodegradable, and readily absorbed into the body's tissues without any significant or lingering side effects. Collagen is an abundant natural polymer which is a fibrous protein which comprises about one-third of the total protein in vertebrates, and which is a component of many tissues, including integument. It has several levels of structural order, the tertiary structure being that of a triple helix. Collagen can be extracted from connective tissue such as cattle hides and tendons in relatively pure form, and reconstituted from dispersions, after which it can be fashioned into membranes, fibers, etc. While collagen obtained in this way can be used for preparing three-dimensional matrix membranes of the present invention in accordance with the method described further below, a preferred material is one of the derivatives of collagen which can function as analogs of the extracellular membrane component of the integument, which plays a key role in wound healing. Using one of these materials as the major polymer component of the matrix membrane of the present invention provides even more beneficial properties in the final integument substitute.

Collagen Derivative Components of the Matrix Membrane Which Can Also Function As Extracellular Matrix Constituents Properly chosen derivatives of collagen can serve as regeneration templates, i.e., they can induce tissue regeneration, and thus wound healing. Features which distinguish these templates from biologically inactive collagens are, e.g., the chemical composition of the polymers making up the matrix, the extent of cross-linking in those polymers, the average diameter of the pores and the spatial distribution of those pores, the proportion of collagen which is present in a highly crystalline form, and the volume fraction of water. Significantly, it is possible to overcome the natural tendency of healing integument to produce only non-physiological connective tissue, i.e., scar tissue, since the dermis does not spontaneously regenerate, by using as a regeneration template a matrix membrane of the present invention. Collagen derivatives suitable for the hydrophilic polymer component which also serve as regeneration templates, are copolymers of collagen and the family of glycosaminoglycans. Examples of the latter are chondroitin 6-sulfate, chondroitin 4-sulfate, heparan sulfate, heparin, dermatan sulfate, and keratan sulfate. The copolymers of these glycosaminoglycans with collagen are graft copolymers, i.e., the glycosaminoglycan chains are grafted onto the collagen, which may be carried out in a straight-forward manner. A coprecipitate of collagen and the selected glycosaminoglycan is formed, and then this condensed state is treated under conditions which will favor formation of covalent bonds between the two polymer components. The coprecipitation requires the presence of sulfate groups on the glycosaminoglycan, and an acid pH. It is theorized that the coprecipitate is an ionic complex formed by the interaction between the anionic sulfate groups of the glycosaminoglycan and the amino groups of the collagen, which would be positively charged under the acidic pH conditions required for coprecipitation.

It is desirable that a significant amount of cross-linking be introduced into the graft copolymers as well; they should be insoluble as well. This insolubility is neither complete nor permanent, but will ensure the short term integrity of the matrix membrane by preventing a too-rapid disintegration of the collagen copolymer component. The collagen and glycosaminoglycan graft coprecipitates can be made insoluble by the simple expedient of drastic dehydration. This can even be accomplished at only moderately elevated temperatures provided that a sufficiently high vacuum is used to achieve the necessary degree of moisture removal. This treatment can also be used to achieve cross-linking of the glycosaminoglycan as well, although dialdehyde crosslinking agents, e.g., glutaraldehyde, are also suitable. Such cross-linking agents have the additional benefit of providing more control over the extent of cross-linking, and thus control over the rate of enzymatic degradation of the collagen glycosaminoglycan graft copolymer matrix. In this way it is possible to obtain implants which will be absorbed into the surrounding tissue over a period of time which has been essentially designed into the implant. It is preferred to use a combination of dehydration and glutaraldehyde to achieve cross-linking of the copolymers. These procedures have the added benefit of sterilizing the copolymers.

Three-Dimensional Matrix Membrane: Asymmetric Pore Structure

The term "three-dimensional" employed herein to modify "matrix membrane", has reference to one of the key features of the inherent structure of the matrix membrane of the present invention. Most membrane materials are essentially two-dimensional in structure. Because the pores of such a filtering membrane retain on average the same dimensions throughout the membrane structure, i.e., their diameters on average are the same in the area of one surface of said membrane as in the area of the opposite surface, their ability to immobilize cellular matter from a suspending medium is essentially limited to two dimensions. As a consequence, the cellular matter tends to become trapped in the pores in the area of the surface of the membrane through which the suspending medium first passes. Further, such membranes are clearly not able to separate and immobilize within them two different cell types, based on different sizes on average of said cell types.

Figure 2:
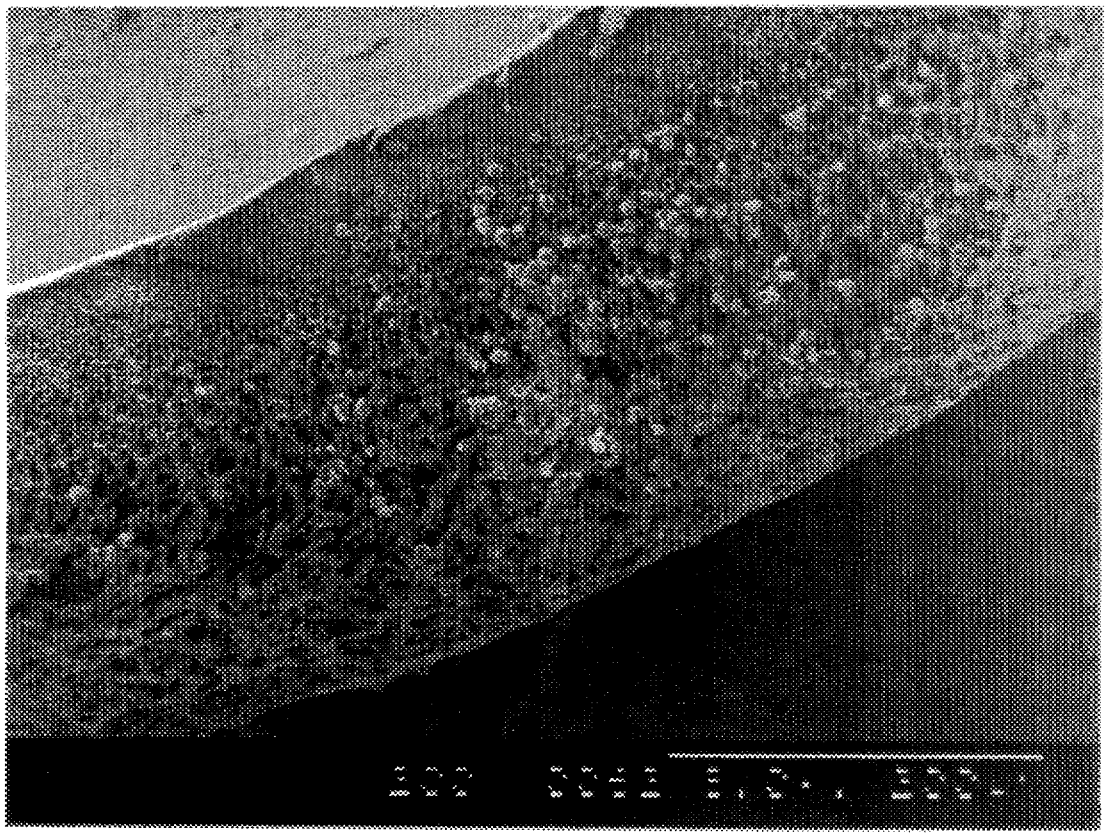
FIG. 2 is a photomicrograph of a portion of the three-dimensional matrix membrane used in the present invention which shows its asymmetrical pore structure and a number of cells which have been isolated and immobilized along a certain pore size stratum of said membrane.
Figure 3:
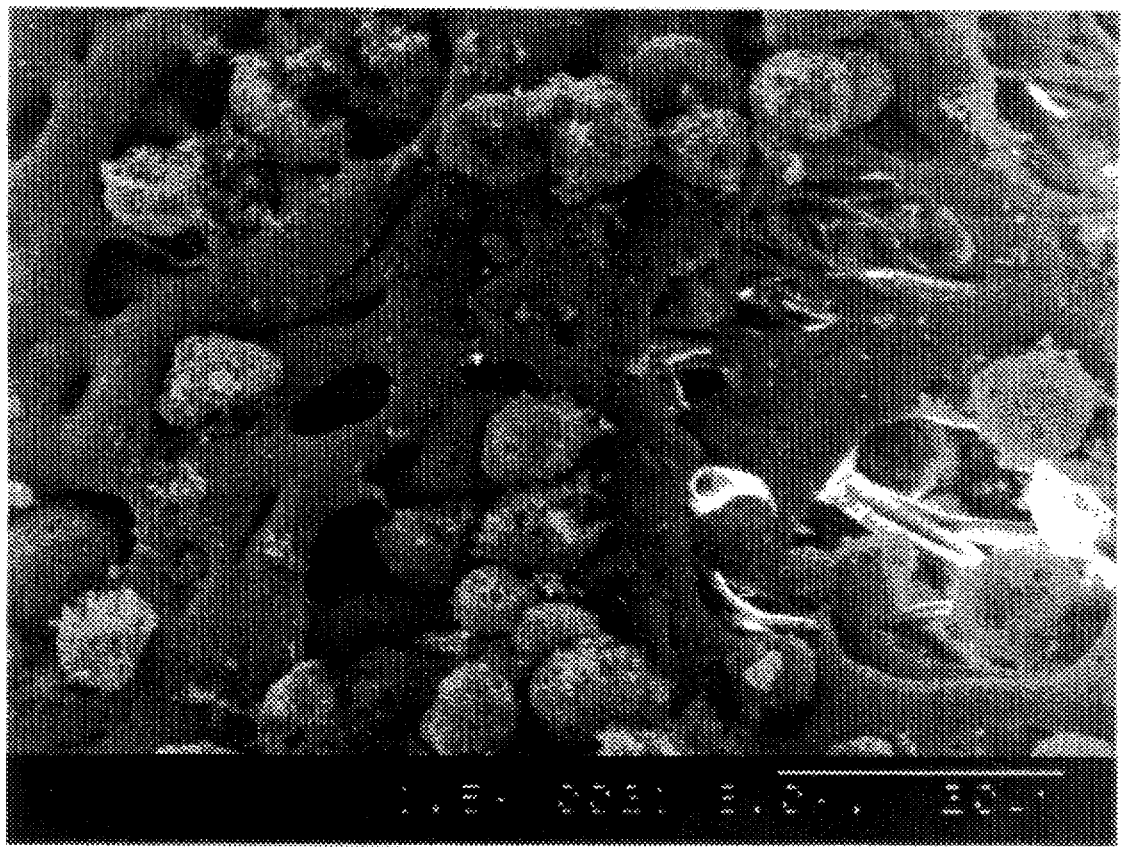
FIG. 3 is a photomicrograph of a portion of the three-dimensional matrix membrane at much greater magnification than in FIG. 1 which shows that cells have been isolated and immobilized without damage or disruption. The "lateral porosity" feature of the three-dimensional structure of the membrane is also shown in this photomicrograph.

The pore structure of the three-dimensional matrix membranes used in the present invention is asymmetrical, i.e., the diameters of the pore openings in the area of one surface of said membrane are on average larger than the diameters on average of the pore openings in the area of the opposite side of said membrane. The internal porous structure is essentially graduated in diameter size from one surface to the other, so that the pores are essentially conical or funnel-shaped in cross-section. This will be understood to be an oversimplification, however, since the porous structure of the three-dimensional matrix membrane resembles that of a sponge, with the labyrinthine interstices taking on the appearance of a three-dimensional web. Nevertheless, the essential character and function of the membrane, in which the dimensions of the porous structure are graduated from one surface of the membrane to the other, is retained and can be clearly seen from the photomicrograph of FIG. 2 thereof which is set forth in the drawings and described herein.

Another essential characteristic of the porous structure of the three-dimensional matrix membrane used in the present invention is what has been referred to herein as "lateral porosity". By this expression is meant the interconnectedness of the porous structure by which the pores traveling from one surface of said membrane to the other are connected to each other by pores or pore openings which travel laterally between them. This characteristic of the porous structure can be clearly seen from the photomicrograph of FIG. 2 thereof which is set forth in the drawings and described herein. In conventional filtering membranes, the porosity of the material from which the membrane is made is usually unidirectional, i.e., the pores run wholly or predominantly parallel to an axis of said membrane. As a consequence, once the pores of such a membrane become occluded by cellular matter, the liquid portion of the suspending medium is no longer able to pass through the membrane. The materials from which the three-dimensional matrix membrane used in the present invention are made are, by contrast, multidirectional or omnidirectional, so that the membrane has an amorphous sponge-like structure. This structure permits the liquid portion of the suspending medium to move through the lateral pore structure when it is obstructed by cellular occluding some pore running parallel to the main flow axis of the membrane. Such co-planar flow allows the suspending medium to pass quickly through the membrane.

The lateral porosity of the membrane is important to the proper functioning of the membrane with regard to the immobilization and establishment therein of the different cellular components of the integument, particularly of the epidermal and dermal layers, which are contained in a suspending medium used to introduce said cellular components into said membrane. As already noted, in conventional filtering membranes, the pores tend to become clogged. This prevents efficient separation and immobilization of the cellular matter which is suspended in the medium, and becomes particularly critical with respect to the immobilization of cellular matter of two different types, i.e., of two different sizes, in this case the epidermal layer cells and dermal layer cells. In order to achieve such separation, it is necessary that all of the suspending medium pass entirely through the membrane. This is achieved by the lateral porosity of the membrane. By using the matrix membranes of the present invention, cells from the various component layers of integument can be isolated, immobilized and cultured into tissue masses, all without disrupting or disturbing those cells and growing tissues in any way. This is essential for producing a integument substitute which, when implanted in the patient, will continue to grow, integrate itself fully into the patient's surrounding integument tissue, result in a minimum amount of scar tissue formation, and be free of agents such as toxic compounds or pathogens which could jeopardize the success of the implant, if not endanger the patient's health.

What is claimed is:

1. A cultured, full-thickness integument substitute implanted in or to be implanted in a patient requiring the same, comprising a three-dimensional matrix membrane with essentially two surfaces, in that the length and width thereof are substantially greater than the thickness thereof which is from about 0.1 mm to about 5 mm, said matrix membrane being non-reactive with respect to cells and components of normal integument; said membrane having pores in the area of a first surface thereof which are directly connected to, but substantially larger on average than those in the area of the opposite surface of said membrane, having a mean pore diameter in the range of from about 50 µm to about 900 µm, said pores having immobilized therein cells and components of a dermal layer of said integument; said membrane having pores in the area of a second surface thereof which are directly connected to but substantially smaller on average than those in the area of the opposite surface of said membrane, having a mean pore diameter in the range of from about 0.5 µm to about 100 µm, said pores having immobilized therein cells and components of an epidermal layer of said integument; said membrane also having a lateral pore structure in the internal space thereof interconnecting said pores which pass from one surface to the other of said membrane, permitting coplanar flow of a liquid or suspension therethrough.

2. A cultured, full-thickness integument substitute according to claim 1 additionally including one or more members selected from the group consisting of the extracellular matrix, basement membrane cells, fibroblasts, anchoring fibrils, and melanocytes.

3. A cultured, full-thickness integument substitute according to claim 2 wherein basement membrane cells are added and are immobilized in pores of said matrix membrane, in a portion thereof located between the portion where the epidermal layer cells and components are immobilized, and the portion where the dermal layer cells and components are immobilized.

4. A cultured, full-thickness integument substitute according to claim 1 wherein said matrix membrane is made from a natural or synthetic polymer, or mixture thereof.

5. A cultured, full-thickness integument substitute according to claim 1 wherein said matrix membrane comprises a hydrophobic polymer matrix to which is attached a hydrophilic polymer.

6. A cultured, full-thickness integument substitute according to claim 5 wherein said hydrophobic polymer is a member selected from the group consisting essentially of polyethylene, polypropylene, polytetrafluoroethylene, polyacrylonitrile, polyvinylidene mono- and difluoride, polyethylene vinylacetate, and polyester; and wherein said hydrophilic polymer is a member selected from the group consisting essentially of nitrocellulose, hydroxypropylcellulose, cellulosic materials and derivatives, collagen, collagenous materials and derivatives, polyvinyl pyrrolidone, polycarbonate, polysulfone/poly (ether sulfone), polyimide/poly(ether imide), and aliphatic polyamides.

7. A cultured, full-thickness integument substitute according to claim 6 wherein said matrix membrane is biodegradable, and said hydrophobic and hydrophilic polymers have introduced therein individual monomers, or segments, or blocks of monomers which are susceptible to degradation by agents to be encountered in said patient's dermal tissues.

8. A cultured, full-thickness integument substitute according to claim 6 wherein said hydrophilic polymer is a graft copolymer of collagen and one or more glycosaminoglycans selected from the group consisting essentially of chondroitin 6-sulfate, chondroitin 4-sulfate, heparan sulfate, heparin, dermatan sulfate, and keratan sulfate.

9. A Cultured, split-thickness integument substitute for either a dermal layer or for an epidermal layer of said integument, implanted in or to be implanted in a patient requiring the same, comprising a three-dimensional matrix membrane with essentially two surfaces, in that the length and width thereof are substantially greater than the thickness thereof which is from about 0.1 mm to about 5 mm, said matrix membrane being non-reactive with respect to cells and components of said integument; in which either pores in the area of a first surface having a mean pore diameter in the range of from about 50 µm to about 900 µm, have immobilized therein cells and components of said dermal layer of said integument, or in which pores in the area of a second, opposite surface having a mean pore diameter in the range of from about 0.5 µm to about 100 µm, have immobilized therein cells and components of said epidermal layer of said integument; wherein said matrix membrane with only dermal layer cells and components will be implanted in a patient having a full-thickness burn or wound, where said membrane will become anchored to said patient's supporting tissue sublayers exposed by said burn or wound; and wherein said matrix membrane with only said epidermal layer will be implanted in a patient as a split thickness allograft or homograft.

10. A surgical kit comprising a sealed container providing a sterile environment, and contained therein a sterilized surgical implant device comprising a cultured, full-thickness or split-thickness integument substitute to be implanted in a patient requiring the same, wherein said three-dimensional mark membrane comprises essentially two surfaces, in that the length and width thereof are substantially greater than the thickness thereof which is from about 0.1 mm to about 5 mm, said matrix membrane being non-reactive with respect to calls and components of said integument; in which either pores in the area of a first surface having a mean pore diameter in the range of from about 50 µm to about 900 µm, have immobilized therein cells and components of a dermal layer of said integument, or in which pores in the area of a second, opposite surface having a mean pore diameter in the range of from about 0.5 µm to about 100 µm, have immobilized therein cells and components of an epidermal layer of said integument, or in which pores in the area of both said first and second surfaces have immobilized therein cells and components of said dermal layer and said epidermal layer, respectively; said membrane also having a lateral pore structure in the internal space thereof interconnecting said pores which pass from one surface to the other of said membrane, permitting co-planar flow of a liquid or suspension therethrough.

11. A method of preparing a cultured, full-thickness integument substitute implanted in or to be implanted in a patient requiring the same, comprising:

A) establishing a three-dimensional matrix membrane with essentially two surfaces, in that the length and width thereof are substantially greater than the thickness thereof which is from about 0.1 mm to about 5 mm, said matrix membrane being non-reactive with respect to cells and components of said integument; said membrane having pores in the area of a first surface thereof which are directly connected to, but substantially larger on average than those in the area of a second, opposite surface of said membrane, said first surface pores having a mean pore diameter in the range of from about 50 µm to about 900 µm; said membrane having pores in said area of said second surface thereof which are directly connected to but substantially smaller on average than those in said area of said first, opposite surface of said membrane, said second surface pores having a mean pore diameter in the range of from about 0.5 µm to about 100 µm; said membrane also having a lateral pore structure in the internal space thereof interconnecting said pores which pass from one surface to the other of said membrane, permitting co-planar flow of a liquid or suspension therethrough;

B) bringing said first surface of said matrix membrane with said larger pores in contact with cells and components of said integument whereby they pass through said matrix membrane, with larger cells and components of a dermal layer of said integument becoming immobilized within said pores in said area of said first surface of said matrix membrane, and with smaller cells and components of an epidermal layer of said integument becoming immobilized within said pores in said area of said second surface of said matrix membrane;

C) culturing said matrix membrane thus seeded with said cells and components of said integument immobilized in different pore areas thereof under conditions favorable to growth of said integument cells, whether in vivo or in vitro, whereby there results a cultured, full-thickness integument substitute already implanted in, or ready for implantation in said patient.

12. A method according to claim 11 wherein for the step of establishing said three-dimensional matrix membrane, the membrane comprises a hydrophobic polymer matrix to which is attached a hydrophilic polymer, wherein said hydrophobic polymer is a member selected from the group consisting essentially of polyethylene, polypropylene, polytetrafluoroethylene, polyacrylonitrile, polyvinylidene mono- and difluoride, polyethylene vinylacetate, and polyester; and wherein said hydrophilic polymer is a member selected from the group consisting essentially of nitrocellulose, hydroxypropylcellulose, cellulosic materials and derivatives, collagen, collagenous materials and derivatives, polyvinyl pyrrolidone, polycarbonate, polysulfone/poly(ether sulfone), polyimide/poly(ether imide), and aliphatic polyamides.

13. A method according to claim 12 wherein said hydrophilic polymer, while in an essentially non-swollen state, is attached to said hydrophobic polymer framework by cross-linking, giving an integrated polymer structure, the pore structure of which may be adjusted accurately by this step.

14. A method according to claim 12 wherein said three-dimensional matrix membrane is prepared by a phase inversion techniques using a hydrophobic polymer material which is soluble in a solvent or solvent mixture; and once said hydrophobic polymer component of said matrix membrane is formed, adding said hydrophilic polymer component by crosslinking said hydrophilic and hydrophobic components using cross-linking agents.

15. A method according to claim 12 wherein said hydrophilic polymer is a graft copolymer of collagen and one or more glycosaminoglycans selected from the group consisting essentially of chondroitin 6-sulfate, chondroitin 4-sulfate, heparan sulfate, heparin, dermatan sulfate, and keratan sulfate.

16. A method according to claim 15 wherein said glycosaminoglycan chains are grafted onto said collagen by forming a coprecipitate of collagen and said glycosaminoglycan, and then treating this condensed state material under conditions which will favor formation of covalent bonds between the two polymer components thereof.

17. A method of preparing a cultured, split-thickness or full-thickness integument substitute implanted in or to be implanted in a patient requiring the same, comprising:

A) establishing a three-dimensional matrix membrane with essentially two surfaces, in that the length and width thereof are substantially greater than the thickness thereof which is from about 0.1 mm to about 5 mm, said matrix membrane being non-reactive with respect to cells and components of said integument; said membrane having pores in the area of a first surface thereof which are directly connected to, but substantially larger on average than those in the area of a second, opposite surface of said membrane, said first surface pores having a mean pore diameter in the range of from about 50 µm to about 900 µm; said membrane having pores in said area of said second surface thereof which are directly connected to but substantially smaller on average than those in said area of said first, opposite surface of said membrane, said second surface pores having a mean pore diameter in the range of from about 0.5 µm to about 100 µm; said membrane also having a lateral pore structure in the internal space thereof interconnecting said pores which pass from one surface to the other of said membrane, permitting co-planar flow of a liquid or suspension therethrough; and then carrying out either or both of the following steps B) and C):

B) bringing said first surface of said matrix membrane with said larger pores in contact with cells and components of a dermal layer of said integument whereby they become immobilized within pores in the area of said first surface of said matrix membrane; and/or C) bringing said second surface of said matrix membrane with said smaller pores in contact with cells and components of an epidermal layer of said integument whereby they become immobilized within pores in the area of said second surface of said matrix membrane; and D) culturing said matrix membrane thus seeded with said cells and components of said dermal and/or epidermal layers of said integument immobilized in different pore areas thereof under conditions favorable to growth of said integument cells, whether in vivo or in vitro, whereby there results a cultured, split thickness and/or full-thickness integument substitute already implanted in, or ready for implantation in said patient.

18. A method of treating a patient requiring integument replacement as the result of burns, trauma or other condition that leaves significant areas of said integument destroyed, so badly damaged that normal recovery is not possible, or vulnerable to invasion by pathogens, comprising applying to an area requiring integument replacement a substitute integument which will enhance the rate of healing and will grow and become integrated into surrounding natural integument layers of said patient which still remain, wherein said integument substitute comprises a three-dimensional matrix membrane with essentially two surfaces, in that the length and width thereof are substantially greater than the thickness thereof which is from about 0.1 mm to about 5 mm, said matrix membrane being non-reactive with respect to cells and components of said integument; said membrane having pores in the area of a first surface thereof which are directly connected to but substantially larger on average than those in the area of a second, opposite surface of said membrane, said first surface pores having a mean pore diameter in the range of from about 50 µm to about 900 µm, said pores having immobilized therein cells and components of a dermal layer of said integument; said membrane having pores in the area of a second surface thereof which are directly connected to but substantially smaller on average than those in said area of said first, opposite surface of said membrane, said second surface pores having a mean pore diameter in the range of from about 0.5 µm to about 100 µm, said pores having immobilized therein cells and components of an epidermal layer of said integument; said membrane also having a lateral pore structure in the internal space thereof interconnecting said pores which pass from one surface to the other of said membrane, permitting co-planar flow of a liquid or suspension therethrough.

* * * * *